United States Patent [19]

Berg

[11] Patent Number: 4,756,803

[45] Date of Patent: * Jul. 12, 1988

[54] SEPARATION OF 2-BUTANOL FROM T-AMYL ALCOHOL BY EXTRACTIVE DISTILLATION

[76] Inventor: Lloyd Berg, 1314 S. Third Ave., Bozeman, Mont. 59715

[ * ] Notice: The portion of the term of this patent subsequent to Dec. 1, 2004 has been disclaimed.

[21] Appl. No.: 788,978

[22] Filed: Oct. 18, 1985

[51] Int. Cl.$^4$ .......................... B01D 3/40; C07C 29/84
[52] U.S. Cl. ......................................... 203/51; 203/60; 203/61; 568/913
[58] Field of Search ............................ 203/51, 61, 60; 568/918, 913

[56] References Cited

U.S. PATENT DOCUMENTS

| | | | |
|---|---|---|---|
| 2,551,584 | 5/1951 | Carlson et al. | 203/51 |
| 2,552,412 | 5/1951 | Drout et al. | 203/84 |
| 2,559,519 | 7/1951 | Smith et al. | 203/64 |
| 2,559,520 | 7/1951 | Smith et al. | 203/64 |
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 2,706,707 | 4/1955 | Morrell et al. | 203/57 |

Primary Examiner—Wilbur Bascomb

[57] ABSTRACT

2-Butanol cannot be completely removed from 2-butanol - t-amyl alcohol mixtures by distillation because of the proximitry of their boiling points. 2-Butanol can be readily removed from mixtures containing it and t-amyl alcohol by using extractive distillation in which the extractive agent is a higher boiling benzoate. Typical examples are methyl benzoate; methyl benzoate and salicylic acid; methyl benzoate, cinnamic acid and hexahydrophthalic anhydride.

9 Claims, No Drawings

SEPARATION OF 2-BUTANOL FROM T-AMYL ALCOHOL BY EXTRACTIVE DISTILLATION

FIELD OF THE INVENTION

This invention relates to a method for separating 2-butanol from t-amyl alcohol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

2-Butanol and t-amyl alcohol are two widely used alcohols in commerce. When they are used as solvents, they frequently end up as mixtures. Whenever practical, it is mandatory to recover the solvent and re-use it. The usual way of recovering liquid components is by distillation in a multiplate rectification column. 2-Butanol boils at 99.5° C., t-amyl alcohol at 102.4° C. and these two have a relative volatility of 1.12 making is very difficult to separate these two by ordinary rectification.

Extractive distillation would be an attractive method of effecting the separation of 2-butanol from t-amyl alcohol if agents can be found that (1) will alter the relative volatility between 2-butanol and t-amyl alcohol, (2) form no azeotrope with 2-butanol or t-amyl alcohol and (3) are easy to recover from t-amyl alcohol, that is boil sufficiently above t-amyl alcohol to make separation by rectification possible with only a few theoretical plates.

Extractive distillation typically requires the addition of an equal amount to twice as much extractive agent as the 2-butanol - t-amyl alcohol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Centigrade degrees or more difference. It is also desirable that the extractive agent be miscible with the t-amyl alcohol otherwise it will form a two phase azeotrope with it and some other method of separation will have to be employed.

Smith, U.S. Pat. No. 2,559,519 described an extractive distillation process to separate n-propanol from 2-butanol using ethylene glycol butyl ether and diethylene glycol ethyl ether as extractive agents. Smith, U.S. Pat. No. 2,559,520 reported 1,3-butanediol as the extractive agent for the same separation. Carlson and Smith, U.S. Pat. No. 2,570,205 reported the use of sulfolane for the n-propanol - 2-butanol separation.

OBJECTIVE OF THE INVENTION

The object of this invention is to provide a process or method of extractive distillation that will enhance the relative volatility of 2-butanol from t-amyl alcohol in their separation in a rectification column. It is a further objective of this invention to identify organic compounds which are stable, can be separated from t-amyl alcohol by rectification with relatively few plates and can be recycled to the extractive distillation column and re-used with little decomposition.

SUMMARY OF THE INVENTION

The objects of this invention are provided by a process for separating 2-butanol from t-amyl alcohol which entails the use of certain oxygenated organic compounds as the agent in extractive distillation.

DETAILED DESCRIPTION OF THE INVENTION

I have discovered that certain oxygenated organic compounds, some individually but principally as mixtures, will effectively enhance the relative volatility between 2-butanol and 2-amyl alcohol and permit the separation of pure 2-butanol from t-amyl alcohol by rectification when employed as the agent in extractive distillation. Table 1 shows the effect of improving the relative volatility in the separation of 2-butanol from t-amyl alcohol. By conventional rectification, 81 theoretical plates or 108 actual plates of 75% efficiency are required to separate each of these two in 99% purity. With an extractive agent such as methyl salicylate as the extractive agent, relative volatility of 1.25, only 41 theoretical plates or 55 actual plates are required for thse alcohols in 99% purity. Thus the number of plates required can be cut almost in half by employing extractive distillation in this separation.

TABLE 1

| Effect of Relative Volatility on the Separation of 2-Butanol From t-Amyl Alcohol | | | |
|---|---|---|---|
| Extractive Agent | Relative Volatility | Theoretical Plates Req'd for 99% Sepn. | Actual Plates, 75% Efficiency |
| None | 1.12 | 81 | 108 |
| Methyl salicylate | 1.25 | 41 | 55 |
| Methyl benzoate, | 1.24 | 43 | 57 |

TABLE 1-continued

Effect of Relative Volatility on the Separation of 2-Butanol From t-Amyl Alcohol

| Extractive Agent | Relative Volatility | Theoretical Plates Req'd for 99% Sepn. | Actual Plates, 75% Efficiency |
|---|---|---|---|
| Benzoic acid | | | |

Table 2 lists compounds, mixtures and approximate proportions that I have found to be effective. The data in Table 2 was obtained in a vapor-liquid equilibriun still. In each case the starting material was the 50—50% 2-butanol - t-amyl alcohol mixture. The ratios are the parts of extractive agent used per part of 2-butanol - t-amyl alcohol mixture. The relative volatilities are listed for each of two ratios employed. The compounds that are effective as extractive distillation agents when used alone are methyl benzoate, benzyl benzoate, butyl benzoate and ortho-hydroxy methyl benzoate (methyl salicylate). The compounds which are effective when used in mixtures of two or more components are benzoic acid, salicylic acid, phthalic anhydride, hexahydrophthalic anhydride, methyl tetrahydrophthalic anhydride and methyl hexahydrophthalic anhydride. The two relative volatilities shown in Table 2 correspond to the two different ratios. For example in Table 2, one part of methyl benzoate with one part of the 2-butanol - t-amyl alcohol mixture gives a relative volatility of 1.23, 6/5 parts of methyl benzoate gives 1.20. In Table 2, one half part of methyl benzoate mixed with one half part of salicylic acid with one part of 2-butanol - t-amyl alcohol mixture gives a relative volatility of 1.24, 3/5 parts of methyl benzoate plus 3/5 parts of salicylic acid gives 1.23.

TABLE 2

Effective Extracive Agents For Separating 2-Butanol From t-Amyl Alcohol

| Compounds | Ratios | | Relative Volatilities | |
|---|---|---|---|---|
| None | — | | 1.12 | |
| Methyl benzoate | 1 | 6/5 | 1.23 | 1.20 |
| Methyl benzoate, Benzoic acid | $(1/2)^2$ | $(3/5)^2$ | 1.24 | 1.25 |
| Methyl benzoate, Cinnamic acid | " | " | 1.20 | 1.25 |
| Methyl benzoate, Hexahydrophthalic anhydride (HHPA) | " | " | 1.20 | 1.18 |
| Methyl benzoate, Methyl hexahydrophthalic anhydride | " | " | 1.31 | 1.23 |
| Methyl benzoate, Salicylic acid | " | " | 1.24 | 1.23 |
| Methyl benzoate, HHPA, Benzoic acid | $(1/3)^3$ | $(2/5)^3$ | 1.25 | 1.21 |
| Methyl benzoate, HHPA, Cinnamic acid | " | " | 1.25 | 1.31 |

TABLE 2-continued

Effective Extracive Agents For Separating 2-Butanol From t-Amyl Alcohol

| Compounds | Ratios | | Relative Volatilities | |
|---|---|---|---|---|
| Methyl benzoate, HHPA, Phthalic anhydride | " | " | 1.15 | 1.15 |
| Methyl benzoate, HHPA, Methyl tetrahydrophthalic anhydride | " | " | 1.20 | 1.12 |
| Methyl benzoate, HHPA, Salicylic acid | " | " | 1.19 | 1.22 |
| Methyl benzoate, Benzoic acid, Methyl hexahydrophthalic anhydride | " | " | 1.16 | 1.15 |
| Methyl benzoate, Benzoic acid, Methyl tetrahydrophthalic anhydride | " | " | 1.16 | 1.13 |
| Benzyl benzoate | 1 | 6/5 | 1.18 | 1.20 |
| Benzyl benzoate, Benzoic acid | $(1/2)^2$ | $(3/5)^2$ | 1.18 | 1.16 |
| Benzyl benzoate, HHPA | " | " | 1.29 | 1.16 |
| Benzyl benzoate, Benzoic acid, HHPA | $(1/3)^3$ | $(2/5)^3$ | 1.22 | 1.17 |
| Benzyl benzoate, Benzoic acid, Salicylic acid | " | " | 1.23 | 1.23 |
| Benzyl benzoate, Cinnamic acid, Methyl salicylate | " | " | 1.15 | 1.18 |
| Benzyl benzoate, HHPA, Salicylic acid | " | " | 1.15 | 1.17 |
| Butyl benzoate | 1 | 6/5 | 1.23 | 1.20 |
| Butyl benzoate, Cinnamic acid | $(1/2)^2$ | $(3/5)^2$ | 1.13 | 1.16 |
| Butyl benzoate, HHPA | " | " | 1.17 | 1.19 |
| Butyl benzoate, Cinnamic acid, HHPA | $(1/3)^3$ | $(2/5)^3$ | 1.22 | 1.13 |
| Butyl benzoate, Cinnamic acid, Methyl hexahydrophthalic anhydride | " | " | 1.17 | 1.15 |
| o-Hydroxy methyl benzoate (Methyl salicylate) | 1 | 6/5 | 1.26 | 1.24 |
| Methyl salicylate, Cinnamic acid | $(1/2)^2$ | $(3/5)^2$ | 1.18 | 1.15 |
| Methyl salicylate, Phthalic anhydride | " | " | 1.16 | 1.13 |
| Methyl salicylate, HHPA | " | " | 1.23 | 1.17 |
| Methyl salicylate, Methyl hexahydrophthalic anhydride | " | " | 1.16 | 1.20 |
| Methyl salicylate, Benzoic acid, HHPA | $(1/3)^3$ | $(2/5)^3$ | 1.15 | 1.18 |
| Methyl salicylate, Cinnamic acid, Phthalic anhydride | " | " | 1.18 | 1.20 |
| Methyl salicylate, Cinnamic acid, HHPA | " | " | 1.24 | 1.17 |
| Methyl salicylate, Cinnamic acid, Methyl hexahydrophthalic anhydride | " | " | 1.21 | 1.19 |

TABLE 3

Data From Runs Made In Rectification Column

| Agent | Time min. | Stillpot At Start | Temp. °C. Sampling | Overhead Temp. When Sampling | Wt. % 2-Butanol | | Relative Volatility |
|---|---|---|---|---|---|---|---|
| | | | | | Overhead | Bottoms | |
| None | 60 | 99 | 99 | 97 | 59.5 | 45 | 1.12 |
| Methyl benzoate, Benzoic acid | 60 | 98 | 117 | 97 | 65 | 44 | 1.20 |
| Methyl benzoate, Benzoic acid | 90 | 98 | 125 | 97.5 | 67 | 44.5 | 1.23 |
| Methyl benzoate, Benzoic acid | 120 | 98 | 132 | 97.5 | 68.5 | 45 | 1.24 |
| | | | | | | | Average = 1.23 |
| Methyl salicylate | 60 | 99 | 116 | 97 | 65 | 43 | 1.22 |
| Methyl salicylate | 90 | 99 | 123 | 97 | 68 | 44 | 1.25 |
| Methyl salicylate | 120 | 99 | 129 | 97 | 69 | 44.5 | 1.26 |
| | | | | | | | Average = 1.25 |

Notes for Table 3

| Agent | Feed, Wt. % 2-BuOH | Agent Rate of Flow, ml/min | Boilup Rate ml/min. | Agent Temp. °C. | Composition of Agent, Wt. % |
|---|---|---|---|---|---|
| Methyl benzoate, Benzoic acid | 50 | 20 | 10-20 | 95 | 50% MeBn |
| Methyl salicylate | 50 | 20 | 10-20 | 95 | 100% MeSal |

One third parts of methyl benzoate plus ⅓ parts of hexahydrophthalic anhydride plus ⅓ parts of cinnamic acid mixed with one part of 2-butanol - t-amyl alcohol mixture gives a relative volatility of 1.25, with 2/5 parts, these three give 1.31. In every example in Table 2, the starting material is a 50—50% mixture in 2-butanol - t-amyl alcohol which possesses a relative volatility of 1.12.

Several of the compounds listed in Table 2 and whose relative volatility had been determined in the vapor-liquid equilibrium still, were then evaluated in a glass perforated plate rectification column possessing 4.5 theoretical plates. The results are listed in Table 3. The 2-butanol - t-amyl alcohol mixture used contained 50% 2-butanol. The first run is with methyl benzoate and benzoic acid as the extractive agent and here the relative volatility of 1.23 is obtained. This compares with 1.24 and 1.25 shown for methyl benzoate and benzoic acid in Table 2, the data for which was obtained in the vapor-liquid equilibrium still. The second run is with methyl salicylate. This agent gives a relative volatility of 1.25 which may be compared with values of 1.26 and 1.24 in Table 2.

THE USEFULNESS OF THE INVENTION

The usefulness or utility of this invention can be demonstrated by referring to the data presented in Tables 2 and 3. All of the successful extractive distillation agents show that 2-butanol can be removed from t-amyl alcohol by means of distillation in a rectification column and that the ease of separation as measured by relative volatility is considerable. Without these extractive distillation agents, very little improvement will occur in the rectification column. The data also show that the most attractive agents will operate at a boilup rate low enough to make this a useful and efficient method of recovering high purity 2-butanol from any mixture with t-amyl alcohol. The stability of the compounds used and the boiling point difference is such that complete recovery is obtainable and recycle possible by a simple distillation and the amount required for make-up is small.

WORKING EXAMPLES

EXAMPLE 1

Twenty-five grams of 2-butanol, 25 grams of t-amyl alcohol and fifty grams of methyl benzoate were charged to an Othmer type glass vapor-liquid equilibrium still and refluxed for 17 hours. Analysis of the vapor and liquid by gas chromatography gave a vapor composition of 56.8% 2-butanol, 43.2% t-amyl alcohol; a liquid composition of 51.7% 2-butanol, 48.3% t-amyl alcohol. This indicates a relative volatility of 1.23. Ten grams of methyl benzoate were added and refluxing continued for another 12 hours. Analysis indicated a vapor composition of 56.8% 2-butanol, 43.2% t-amyl alcohol; a liquid composition of 52.4% 2-butanol, 47.6% t-amyl alcohol which is a relative volatility of 1.20.

EXAMPLE 2

Fifty grams of the 2-butanol - t-amyl alcohol mixture, 25 grams of methyl benzoate and 25 grams of salicylic acid were charged to the vapor-liquid equilibrium still and refluxed for 16 hours. Analysis indicated a vapor composition of 49.1% 2-butanol, 50.9% t-amyl alcohol; a liquid composition of 43.9% 2-butanol, 56.1% t-amyl alcohol which is a relative volatility of 1.24. Five grams of methyl benzoate and five grams of salicylic acid were added and refluxing continued for another ten hours. Analysis indicated a vapor composition of 49.5% 2-butanol, 50.5% t-amyl alcohol; a liquid composition of 44.4% 2-butanol, 55.6% t-amyl alcohol which is a relative volatility of 1.23.

EXAMPLE 3

Fifty grams of the 2-butanol - t-amyl alcohol mixture, 17 grams of cinnamic acid, 17 grams of hexahydrophthalic anhydride and 17 grams of methyl benzoate were charged to the vapor-liquid equilibrium still and refluxed for 15 hours. Analysis indicated a vapor composition of 39.9% 2-butanol, 60.1% t-amyl alcohol; a liquid composition of 34.7% 2-butanol, 65.3% t-amyl alcohol which is a relative volatility of 1.25. Three grams each of cinnamic acid, hexahydrophthalic anhydride and methyl benzoate were added and refluxing continued for another eleven hours. Analysis indicated a vapor composition of 37.5% 2-butanol, 62.5% t-amyl alcohol and a liquid composition of 31.4% 2-butanol, 68.6% t-amyl alcohol which is a relative volatility of 1.31.

EXAMPLE 4

A glass perforated plate rectification column was calibrated with ethylbenzene and p-xylene which possesses a relative volatility of 1.06 and found to have 4.5 theoretical plates. A solution of 200 grams of 2-butanol and 200 grams of t-amyl alcohol was placed in the stillpot and heated. When refluxing began, an extractive agent consisting of 50% methyl benzoate and 50% benzoic acid was pumped into the column at a rate of 20 ml/min. The temperature of the extractive agent as it entered the column as 95° C. After establishing the feed rate of the extractive agent, the heat input to the 2-butanol - t-amyl alcohol in the stillpot was adjusted to give a reflux rate of 10–20 ml/min. After one hour of operation, overhead and bottoms samples of approximately two ml. were collected and analysed by gas chromatography. The overhead analysis was 65% 2-butanol, 35% t-amyl alcohol. The bottoms analysis was 44% 2-butanol, 56% t-amyl alcohol. Using these compositions in the Fenske equation, with the number of theoretical plates in the column being 4.5, gave an average relative volatility of 1.20 for each theoretical plate. After 1.5 hours of total operating time, the overhead and bottoms samples were again taken and analysed. The overhead composition was 67% 2-butanol, 33% t-amyl alcohol and the bottoms composition was 44.5% 2-butanol, 55.5% t-amyl alcohol. This gave an average relative volatility of 1.23 for each theoretical plate. After two hours of total operating time, the overhead and bottoms samples were again taken and analysed. The overhead composition was 68.5% 2-butanol, 31.5% t-amyl alcohol and the bottoms analysis was 45% 2-butanol, 55% t-amyl alcohol. This gave an average relative volatility of 1.24 for each theoretical plate.

EXAMPLE 5

A solution of 200 grams of 2-butanol and 200 grams of t-amyl alcohol was placed in the stillpot of the same column used in example 4 and heat applied. When refluxing began, an extractive agent comprising pure methyl salicylate was fed to the top of the column at a feed rate of 20 ml/min. and a temperature of 95° C. After establishing the feed rate of the extractive agent, the heat input to the 2-butanol - t-amyl alcohol in the stillpot was adjusted to give a total reflux rate of 10–20 ml/min. Having established the reflux rate, the column was allowed to operate for an hour. After one hour of steady operation, overhead and bottoms samples of approximately two ml. were collected and analysed by gas chromatography. The overhead analysis was 65% 2-butanol, 35% t-amyl alcohol and the bottoms analysis was 43% 2-butanol, 57% t-amyl alcohol. Using these compositions in the Fenske equation with the number of theoretical plates in the column being 4.5, gave an average relative volatility of 1.22 for each theoretical plate. After 1.5 hours of total operation, the overhead and bottoms were again taken and analysed. The overhead composition was 68% 2-butanol, 32% t-amyl alcohol and the bottoms composition was 44% 2-butanol, 56% t-amyl alcohol. This gave an average relative volatility of 1.25 for each theoretical plate. After two hours of total operation, the overhead and bottoms were again taken and analysed. The overhead composition was 69% 2-butanol, 31% t-amyl alcohol and the bottoms composition was 44.5% 2-butanol, 55.5% t-amyl alcohol. This gave an average relative volatility of 1.26 for each theoretical plate.

What is claimed is:

1. A method for recovering 2-butanol from a mixture of 2-butanol and t-amyl alcohol which comprises distilling a mixture of 2-butanol and t-amyl alcohol in a rectification column in the presence of about one to two parts of extractive agent per part of 2-butanol - t-amyl alcohol mixture, recovering 2-butanol as overhead product and obtaining the extractive agent and t-amyl alcohol from the stillpot, the extractive agent comprises at least a benzoate containing from eight to fourteen carbon atoms.

2. The method of claim 1 in which the extractive agent comprises methyl benzoate.

3. The method of claim 1 in which the extractive agent comprises ortho hydroxymethyl benzoate (methyl salicylate).

4. The method of claim 1 in which the extractive agent comprises benzyl benzoate.

5. The method of claim 1 in which the extractive agent comprises butyl benzoate.

6. A method for recovering 2-butanol from a mixture of 2-butanol and t-amyl alcohol which comprises distilling a mixture of 2-butanol and t-amyl alcohol in a rectification column in the presence of about one to two parts of extractive agent per part of 2-butanol - t-amyl alcohol mixture, recovering 2-butanol as overhead product, obtaining the extractive agent and t-amyl alcohol from the stillpot, the extractive agent comprises a benzoate containing from eight to fourteen carbon atoms and at least one material from the group consisting of benzoic acid, cinnamic acid, salicylic acid, phthalic anhydride, hexahydrophthalic anhydride, methyl hexahydrophthalic anhydride and methyl tetrahydrophthalic anhydride.

7. The method of claim 6 in which the extractive agent comprises ortho-hydroxy methyl benzoate (methyl salicylate) and at least one material from the group consisting of benzoic acid, cinnamic acid, phthalic anhydride, hexahydrophthalic anhydride and methyl hexahydrophthalic anhydride.

8. The method of claim 6 in which the extractive agent comprises benzyl benzoate and at least one material from the group consisting of benzoic acid, cinnamic acid, salicylic acid, methyl salicylate and hexahydrophthalic anhydride.

9. The method of claim 6 in which the extractive agent comprises butyl benzoate and at least one material from the group consisting of cinnamic acid, hexahydrophthalic anhydride and methyl hexahydrophthalic anhydride.

* * * * *